(12) United States Patent
Dowding-Young (10) Patent No.: US 10,575,080 B2
(45) Date of Patent: Feb. 25, 2020

(54) AUDIO AND VISUAL SHIELD AND SYSTEM COMPRISING SAME

(71) Applicant: SILENTMODE LIMITED, Hong Kong (HK)

(72) Inventor: Bradley Dowding-Young, Hong Kong (CN)

(73) Assignee: SILENTMODE LIMITED, Admiralty (HK)

( * ) Notice: Subject to any disclaimer, the term of this patent is extended or adjusted under 35 U.S.C. 154(b) by 0 days.

(21) Appl. No.: 16/181,871

(22) Filed: Nov. 6, 2018

(65) Prior Publication Data

US 2019/0149903 A1    May 16, 2019

(30) Foreign Application Priority Data

Nov. 15, 2017 (HK) ..................................... 1711875

(51) Int. Cl.
*A61F 9/04* (2006.01)
*H04R 1/10* (2006.01)

(52) U.S. Cl.
CPC ........... *H04R 1/1008* (2013.01); *A61F 9/045* (2013.01); *H04R 1/105* (2013.01); *H04R 1/1041* (2013.01); *H04R 1/1091* (2013.01); *H04R 2420/07* (2013.01)

(58) Field of Classification Search
CPC ........ H04R 1/02; H04R 1/1091; H04R 1/026; A61F 9/04; A61F 11/12; A61F 9/026; A42B 1/00; A42B 1/061; A42B 1/068; A42B 1/245
See application file for complete search history.

(56) References Cited

U.S. PATENT DOCUMENTS

| | | | |
|---|---|---|---|
| 7,202,774 B2 * | 4/2007 | Hoyle | A61F 9/04 2/6.7 |
| 2012/0131726 A1 * | 5/2012 | Schenk | A61F 9/04 2/173 |
| 2016/0120253 A1 * | 5/2016 | Schenk | A47G 9/10 2/173 |
| 2017/0264994 A1 * | 9/2017 | Gordon | H04R 1/1091 |
| 2018/0125700 A1 * | 5/2018 | Ray | A61M 16/202 |
| 2019/0098392 A1 * | 3/2019 | Abreu | G02C 3/003 |
| 2019/0110927 A1 * | 4/2019 | Schwarz | A61F 9/04 |

FOREIGN PATENT DOCUMENTS

| | | |
|---|---|---|
| CN | 205126559 U | 4/2016 |
| CN | 105796233 | 7/2016 |

\* cited by examiner

*Primary Examiner* — Disler Paul (74) *Attorney, Agent, or Firm* — Ladas & Parry, LLP; Melvin Li (57) ABSTRACT

One aspect of the present invention is concerned with a combination ear and eye shield. The shield has a) an elongate and continuous body wearable by a user defining, in use, an outwardly facing surface and an inwardly facing surface, b) a pair of speakers, c) an audio signal transceiver connectable to the speakers for transmitting signals thereto, and d) a power supply to power the transceiver and/or the speakers. The elongate body includes ear covering regions to cover both the ears, and eye covering regions for covering both the eyes. The transceiver is wirelessly communicable with an external device for receiving signals of desired sound or music. The speakers are removably connectable to and locus changeable along the body such that the speakers are adjustable in position adjacent the ears of a user.

16 Claims, 11 Drawing Sheets

AUDIO AND VISUAL SHIELD AND SYSTEM COMPRISING SAME

CROSS REFERENCE TO RELATED APPLICATION

This application claims priority from earlier filed Hong Kong Patent Application No. 17111875.8 filed Nov. 15, 2017, the contents of which, in its entirety, is hereby expressly incorporated herein.

FIELD OF THE INVENTION

The present invention is concerned with an ear and eye shield and an audio and visual to shield system comprising same.

BACKGROUND OF THE INVENTION

In the 21th century, human civilization has advanced to a state where access of information and communication has become easy, and unfortunately almost too easy. Many individuals have multiple electronic devices such as laptops, tablets, mobile phones, etc. which allow them to be reachable any time of the day. In the past, when most individuals are off duty from work it means really off duty. Now, when individuals are off duty from work, they are not really off duty but rather still "on call" or "in stand-by mode" via mobile devices. This technological trend is causing excessive stress to some individuals. For this reason, knowingly or unknowingly there is a demand of escape means which can allow individuals to break away from a seemingly non-stoppable communications or uncontrollable stimulations from the surroundings.

The present invention seeks to assist individuals to "unplug" from excessive stimulations from the surroundings, or at least to provide an alternative to the public.

SUMMARY OF THE INVENTION

According to a first aspect of the present invention, there is provided a combination ear and eye shield comprising:—
  a) an elongate and continuous body wearable by a user defining, in use, an outwardly facing surface and an inwardly facing surface;
  b) a pair of speakers;
  c) an audio signal transceiver connectable to the speakers or transmitting audio signals thereto; and
  d) a power supply to power the transceiver and/or the speakers;
  wherein:—
  i) the elongate body includes ear covering regions to cover both the ears of a user, and eye covering regions for covering both the eyes of the user;
  ii) the transceiver is wirelessly communicable with an external device for receiving audio signals of desired sound or music; and
  iii) the speakers are removably connectable to and locus changeable along the body such that the speakers are adjustable in position adjacent the ears of a user.

Preferably, the elongate body may be configurable to assume a first configuration with a straightened profile, or a second configuration, and wherein in the first configuration opposite lateral ends the body may be disengaged. The shield may comprise a closure member, wherein in the second configuration the body may be closed by the closure member for connecting or otherwise closing the opposite lateral ends thus to allow the shield to form a closed loop surrounding both the ears and the eyes of a user.

Suitably, the shield may comprise a first fastening means for removable connection of the speakers to the body. The first fastening means may be in the form of hook structures and cooperative coarse/loop structures on the speakers and the body, respectively, or vice versa. The body may be provided with a plurality of recesses or pockets along the length thereof for accommodating the speakers.

Advantageously, the shield may comprise a second fastening means for stowing the transceiver, wherein the fastening means may be in the form of a pouch sized and shaped to fit the transceiver.

The shield may comprise a first fastening means for removable connection of the speakers to the body and a second fastening means for stowing the transceiver, wherein, in the first configuration, the eye covering regions may be interposed between the ear covering regions or speakers.

In an embodiment, in the first configuration, the transceiver may be positioned at a distal end of the body.

In one embodiment, the body may be provided with an eye covering cushion, the cushion being removably connectable to the inwardly facing surface of the body and configured to contact the eyes and/or the ears. The speakers may be interposed between the body and the cushion.

Preferably, the cushion may have an elongate profile and provided with first and second openings on opposite distal ends thereof, the openings may be sized and shaped to receive the speakers and/or to position over the ears in use. The cushion may be provided with third and fourth openings defining a rim and sized and shaped to fit around eye sockets of the eyes in use.

In a preferred embodiment, the power supply may be n the form of a battery, wherein the battery is chargeable.

Suitably, in the second configuration, the speakers may be arranged on opposite sides of the loop shaped shield.

According to a second aspect of the present invention, there is provided a combination ear and eye shield comprising:—
  a) an elongate and continuous body wearable by a user defining, in use, an outwardly facing surface and an inwardly facing surface;
  b) at least one speaker;
  c) an audio signal transceiver connectable to the speaker for transmitting audio signals thereto; and
  d) a power supply to power the transceiver and/or the speaker;
  wherein:—
  i) the elongate body includes ear covering regions to cover both the ear, and eye covering regions for covering both the eyes;
  ii) the transceiver is wirelessly communicable with an external device for receiving audio signals of desired sound or music; and
  iii) the speaker is removably connectable to and locus changeable along the body whereby the speaker is adjustable in position adjacent one of the ears of a user or at a position desired by the user.

According to a third aspect of the present invention, there is provided an audio and visual shield system comprising,
  a) a combination ear and eye shield as claimed in any of Claims 1 to 16; and
  b) an or the external electronic or portable device communicable with the transceiver;
  wherein the external device stores sound or music files or access to sound or music files in a remote location, and acts as an interface via which a user can control which of sound or music files is played and thus broadcasted by the speakers.

Preferably, the external device may be a mobile phone or a tablet. The external device may comprise or be loaded with an application acting as an interface via which, a user can control the shield or system.

DESCRIPTION OF THE DRAWINGS OF PREFERRED EMBODIMENTS OF THE INVENTION

Some embodiments of the present invention will now be explained, with reference to the accompanied drawings, in which:—

DETAILED DESCRIPTION OF PREFERRED EMBODIMENTS OF THE INVENTION

The present invention is concerned with an audio and visual system, comprising a combination ear and eye mask in the form of a shield.

Figure 1:
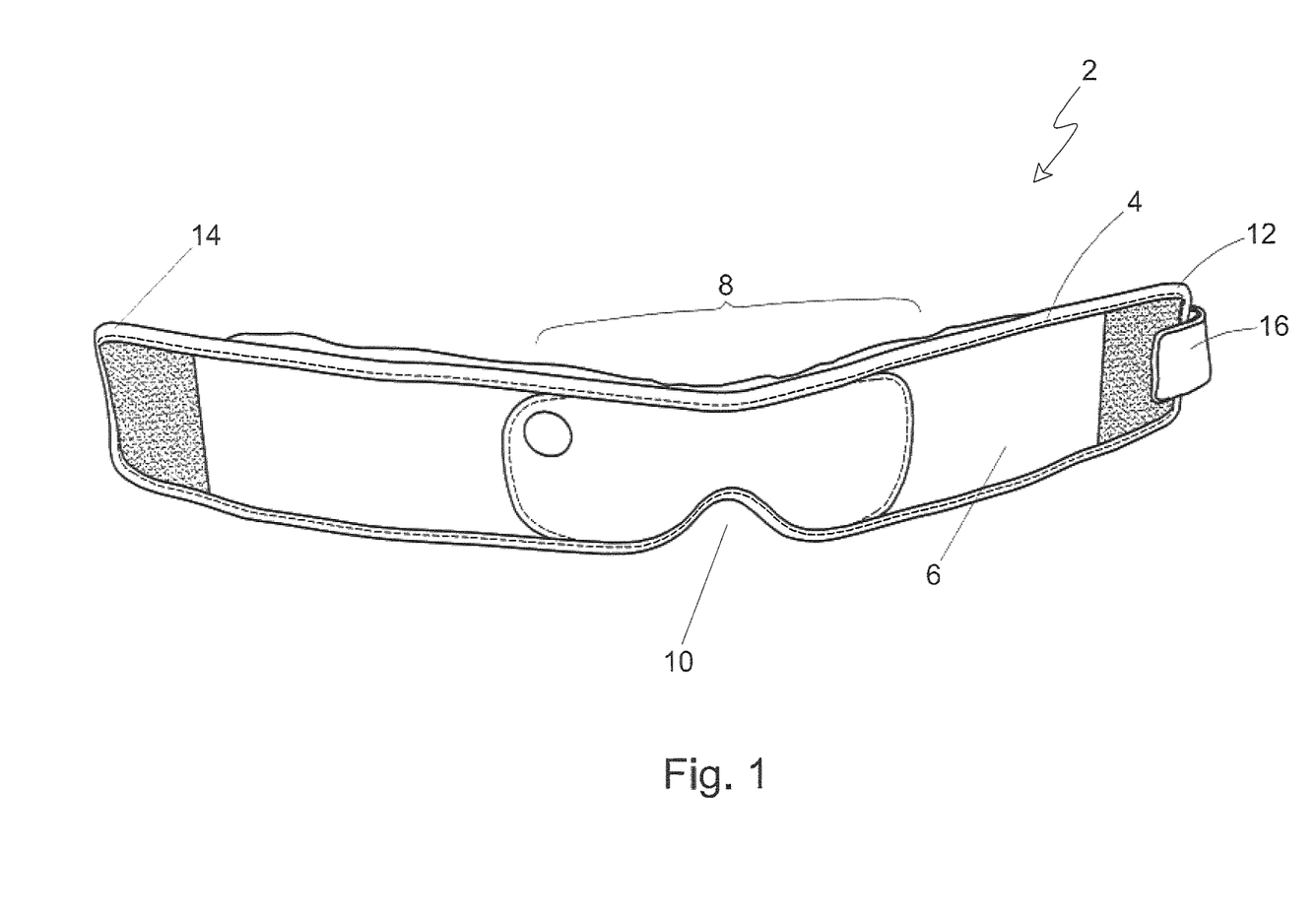
FIG. 1 is a front perspective view of a first embodiment of a combination ear and eye shield according to the present invention, and assuming a first configuration.
Figure 2:
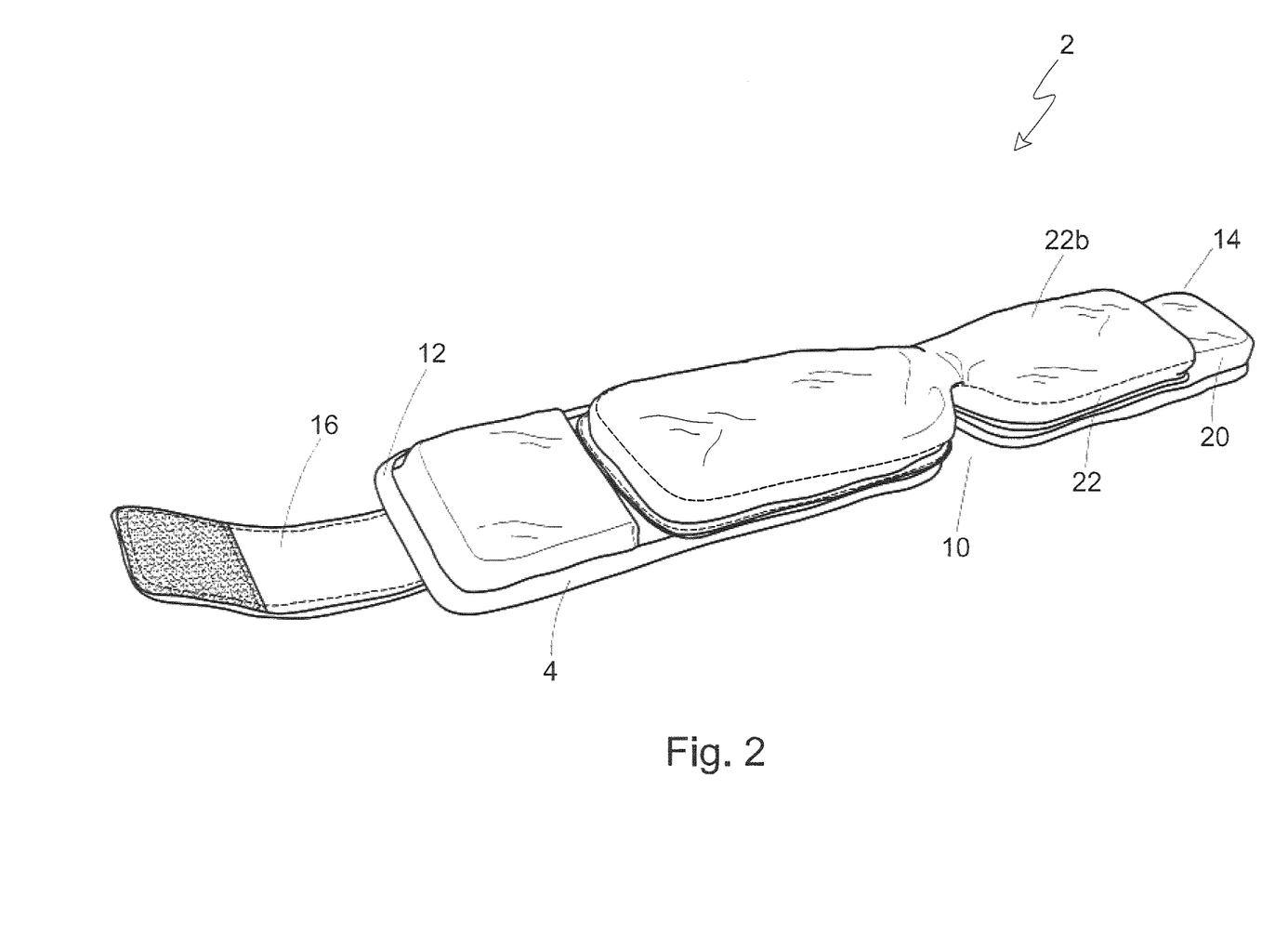
FIG. 2 is a rear perspective view of the shield of FIG. 1.
Figure 3:
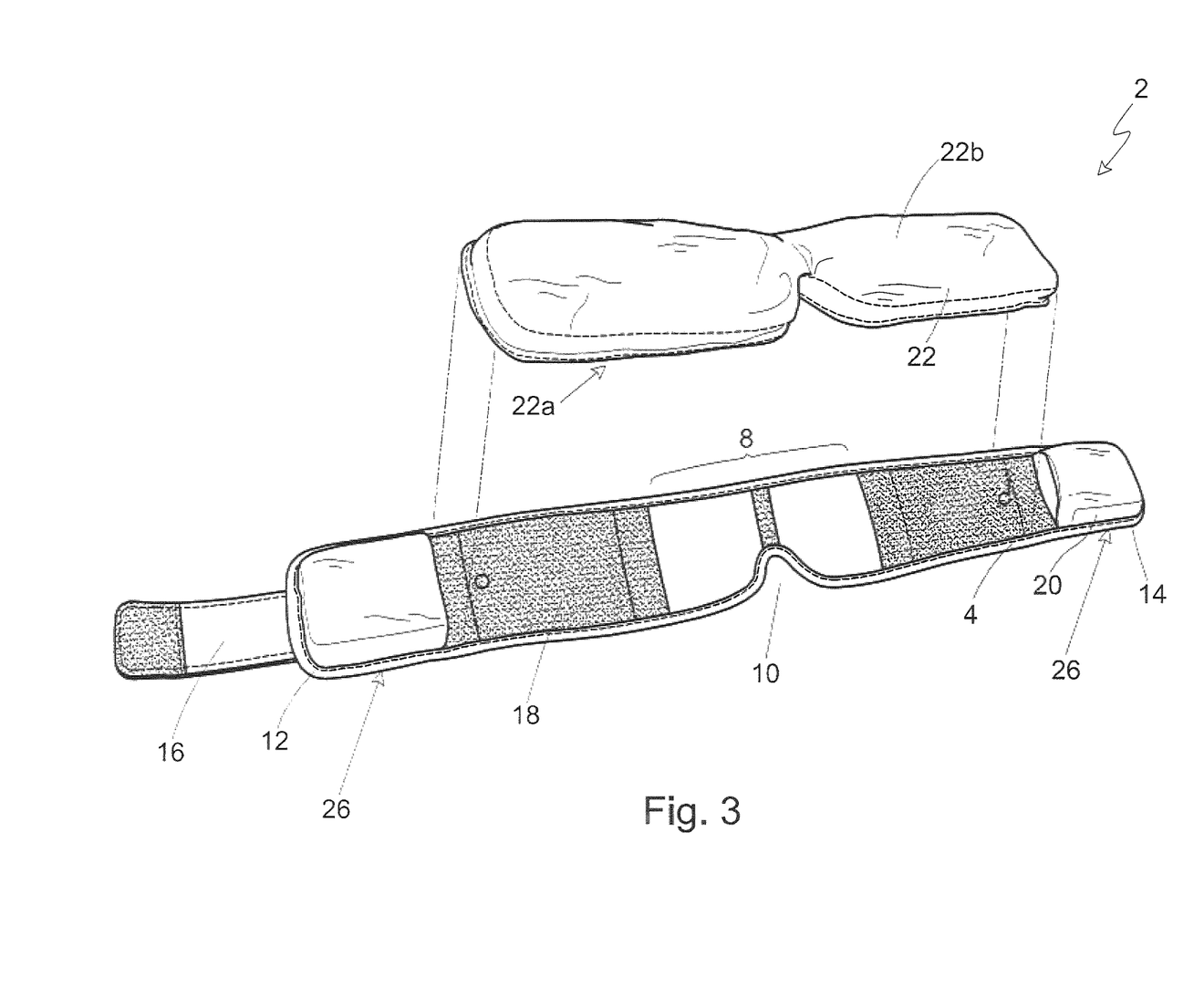
FIG. 3 is a schematic view of the shield of FIG. 1, with a cushion thereof positioned away from a main body of the shield but with speakers of the shield not illustrated.

FIGS. 1-3 shows a first embodiment of a combination ear and eye shield, generally designated 2, in accordance with the present invention.

FIG. 1 is a front perspective view of the shield. The shield has an elongate profile with a laterally extending body 4. The body 4 includes an outer layer made of fabric and an inner layer made of soft foam of ethylene-vinyl acetate (EVA). In a preferred embodiment, the thickness of the inner soft foam layer is substantially 3 mm although the workable thickness is 2-4 mm. This thickness balances the provision of sufficient comfort and yet would not introduce excessive bulkiness to the shield in the context of ear/eye shield. The body 4 defines an outwardly facing surface 6 when in normal use. The outwardly facing surface has a middle region 8 for covering the eyes of user. With the outer fabric layer and the inner memory foam layer, the body 4 can not only provide contact comfort but also better block light from penetrating the shield 2. The middle region 8, or eye covering region, has a thickened (or denser) construction. The thickened construction is achieved by way of an additional layer of light blocking fabric. The middle region 8 has a cut-out portion 10 at its lower end to accommodate the nose of a user in use. The elongate body 4 has opposite lateral ends 12, 14. One end 12 of the body 4 is provided with a bridging member 16 in the form of a flap fixedly secured thereto. The bridging member 16 and the opposite lateral end 14 are provided with hook structures and cooperative coarse/loop structures or vice versa. With these structures, it is envisaged that the opposite ends are removably connectable together. In other words, the bridging member 16, and the hook and cooperative coarse/loop structures act as a connection means to connect the free ends 12, 14 of the body 4.

In this embodiment, the height of the body 4 is substantially 80 mm, respectively, although studies leading to the present invention have shown that the workable length may range from 64-96 mm.

FIGS. 2 and 3 show the body 4 defining an inwardly facing surface 18 when in normal use. This figure further illustrates that the body 4 is provided with a pouch 20 and a cushion 22. The pouch 20 acts a fastener to accommodate and secure a transceiver (not shown) to the body 4. Further details of such transceiver (not shown) will be depicted later in the following.

The cushion 22 is similar to the body 4 in that it has an elongate profile. In this embodiment, the cushion 22 is however different from the body 4 in that it is shorter in length and made of different materials than the body 4. The body 4 at least on the outwardly facing surface 6 is made of a material or fabric different from the cushion 22. Specifically, the outwardly facing surface 6 of the body 4 is made of a fabric that is opaque and thus acts a light blocker. The cushion 22 on the other hand is softer in texture thus acting to provide contact comfort to the face or around the head of a user. Again in this embodiment, the cushion 22 includes an inner cushioning member and an outer sleeve enveloping the inner cushioning member. Although not shown in FIG. 2, the inner cushioning member is made with a configuration with curvature that fits around the eye sockets and ears of a user. In other embodiments, the cushion 22 may be made of an integral component formed from one material.

In this embodiment, the length and height of the cushion 22 are substantially 450 mm and 89.2 mm, respectively, although studies shown that the workable length may range from 360-540 mm and 71.4-107 mm. Due to the taller height, in use the cushion 22 actually extends and protrudes upwardly and downwardly beyond the body 4 and is thus visible from the surroundings.

FIG. 3 is an exploded view showing the shield 2 (although electronics thereof are not shown). This figure shows the shield 2 divided into different zones or regions. The middle regions 8 are for eye covering while the end regions 26 are for ear covering. Stich lines 28 are provided partly to improve and to secure structures of the body 4, and partly to act as means to assist the body to bend or fold during use when worn by a user. The cushion 22 is provided with an outwardly facing surface 22a and an inwardly facing surface 22b. The outwardly facing surface 22a of the cushion 22 is removably adherable to the inwardly facing surface 18 of the body 4 so that the body 4 and the cushion 22 becomes one connected member when worn by a user. In this embodiment, the connection means that allows the cushion to engage with the body are hook structures and cooperative coarse/loop structures, respectively, or vice versa, e.g. Velcro type connection means. Alternatively, other connection means that does not hinder the comfort or curvature of the body 4 may be used.

Figure 4:
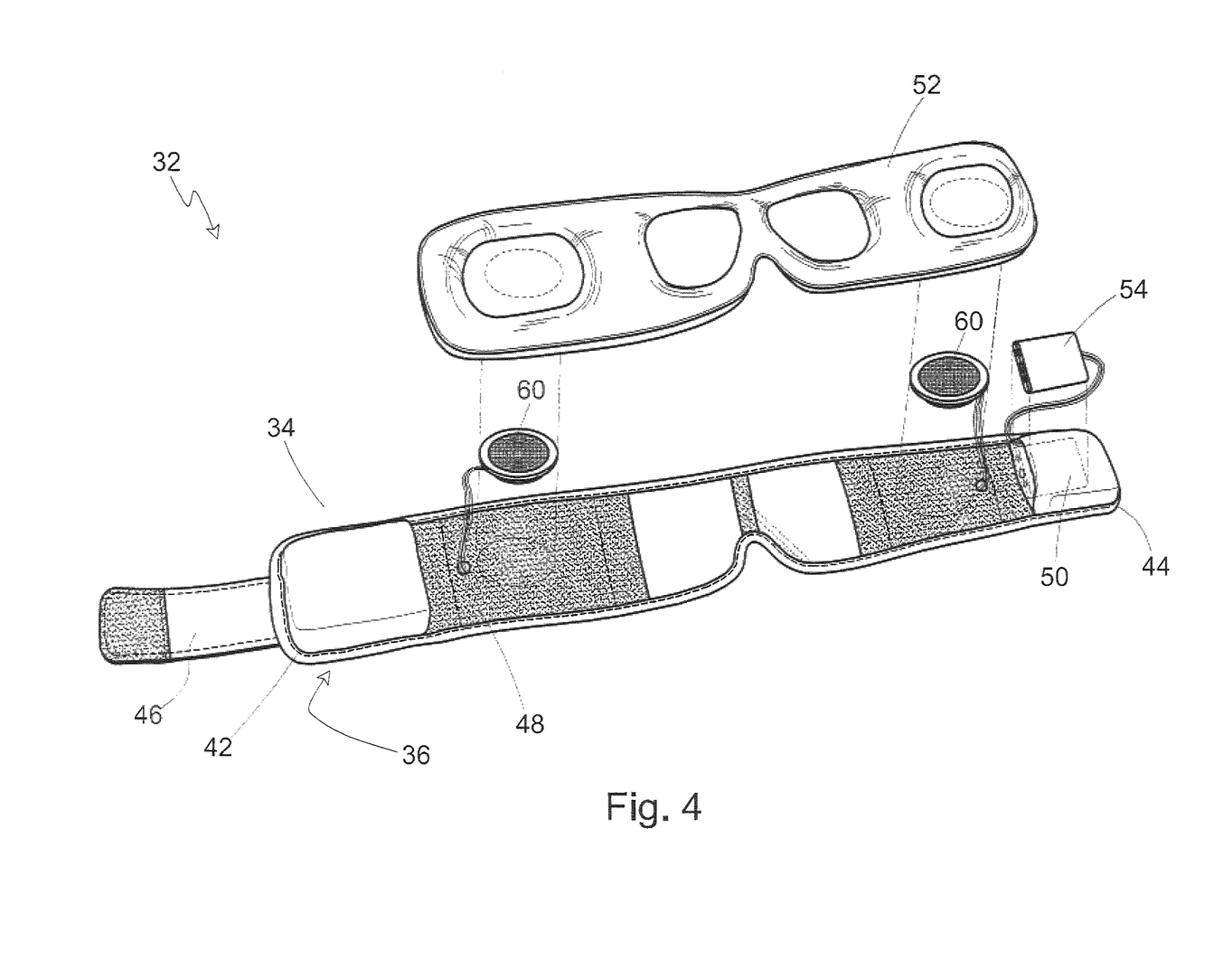
FIG. 4 is an exploded view of a second embodiment of a combination ear and eye shield according the present invention.

FIGS. 4-6C illustrate another embodiment of a shield in accordance with the present invention. The shield, generally designated 32, likewise has an elongate body 34 defining an outwardly facing surface 36 and an inwardly facing surface 48. The body 34 is provided with a transceiver 54 and a pair of speakers 60. The body 34 is also provided with a pouch 50 located at one end 44 thereof for securing and receiving the transceiver 54. The other end body is provided with a pad. FIG. 4 shows that there are provided eye covering regions positioned between the ear covering regions. The speakers 60 are removably connectable to the inwardly facing surface 48 of the body 4. It can thus be envisaged that the location of speakers can be adjusted along the lateral length of the body 4 before use as desired by the user. The speakers 60 and the transceiver 54 are connected by electrical wiring for supplying audio signal from the transceiver 54 to the speakers 60. Most of the wiring is fitted and concealed in the body 4. The body 4 is likewise provided with a bridging member 46 for connecting opposite ends of the body 4. In this embodiment, a connection means that allows the speakers to engage with the body is likewise hook structures and cooperative coarse/loop structures, respectively, or vice vera, e.g. Velcro type connection means. Alternatively, the inwardly facing surface 48 may be provided with one or more slots for receiving the speakers 60 so that the speakers 60 are position adjustable as desired by a user.

Similar to the shield 2, the shield 32 also includes an elongate cushion 52. The cushion 52 is however somewhat different. Instead of being made of an inner soft member enveloped by an outer sleeve, the cushion 52 is essentially made of an integral material of memory foam. Further, the cushion 52 is provided with two explicit and visible openings at opposite distal ends and two further other openings in the middle between the openings at the distal ends. The end openings are configured to position next to the ears and the middle openings are configured to position over the eyes when the shield is worn by a user. Similar to the cushion 22, an outwardly facing surface of the cushion 52 is removably adherable to the inwardly facing surface of the body 34 so that the body 34 and the cushion 52 becomes one connected member when worn by a user.

Figure 5:
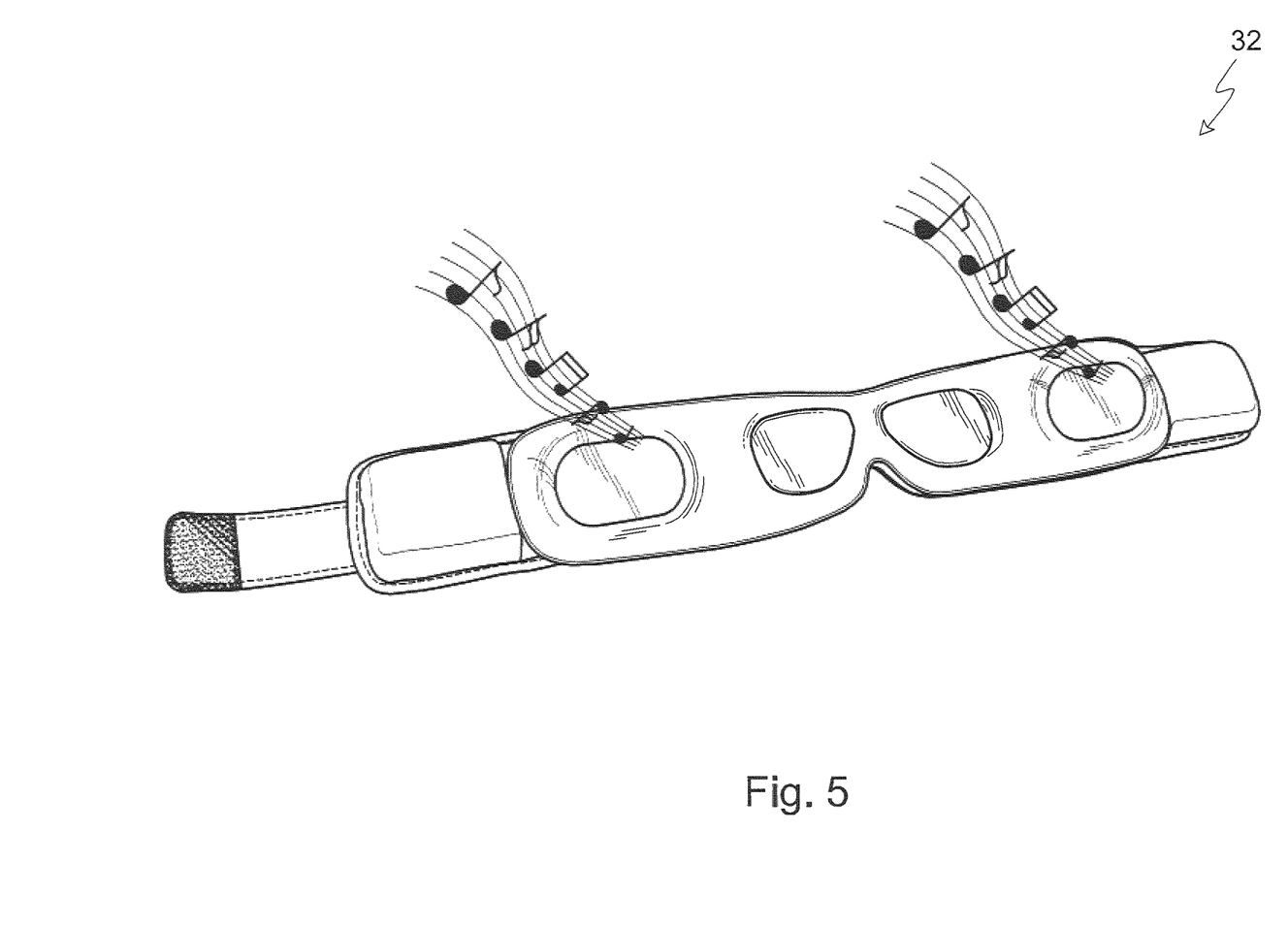
FIG. 5 is a schematic view of the shield of FIG. 4, illustrating sound or music playing by the shield in use.

FIG. 5 shows the shield 32 in an assembled configuration. Regions of the middle openings are for engagement around the eyes, regions of the end openings are for engagement of the ears, the pouch in which the transceiver resides and the pad are arranged at the opposite far ends.

Figure 6A:
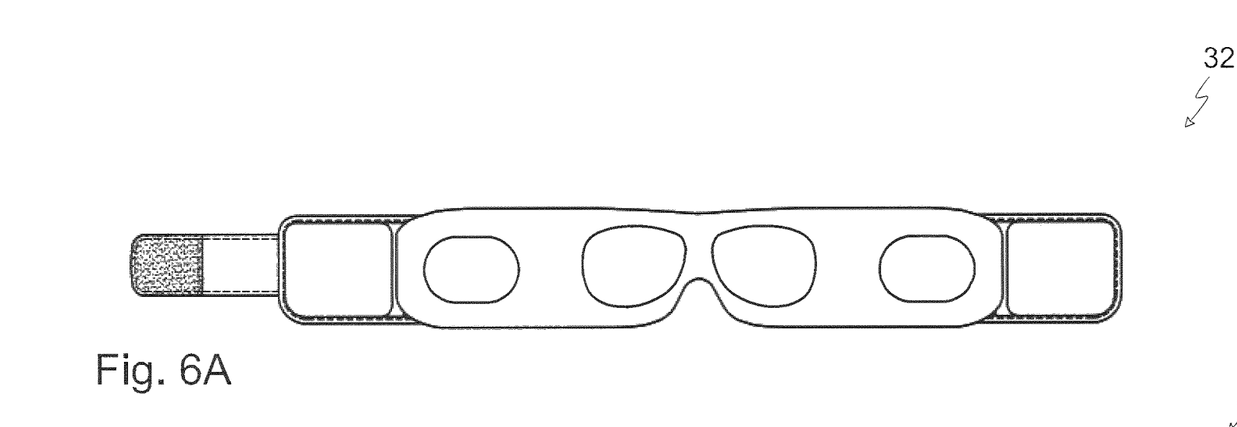
FIGS. 6A, 6B and 6C are rear view, front view and across section view of the shield of FIG. 5.
Figures 6B, 6C:
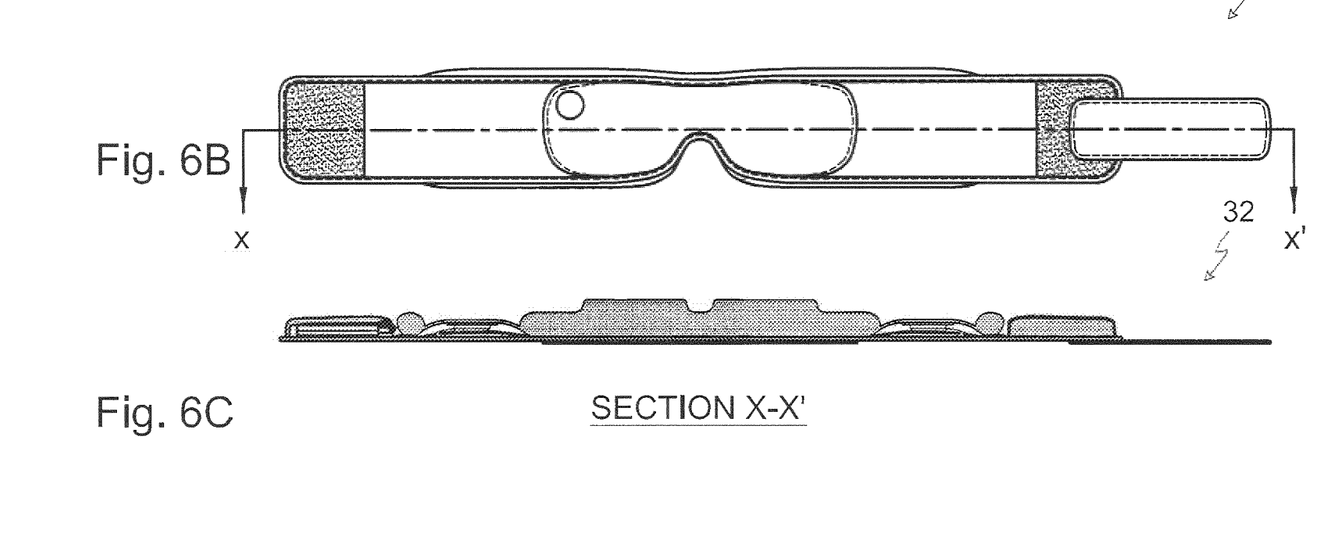

FIG. 6A and FIG. 6B show an inwardly facing surface and an outwardly facing surface the shield 2, respectively. FIG. 6C is a cross section view taken at X-X of FIG. 6B. It is to be noted that when the shield 2 assumes an extended or straightened configuration, the outwardly facing surface is general flat while the inwardly facing surface defines a specific contour. Specifically, the regions around the middle openings are thickened to enhance contact around the eyes, whereby to achieve a better insulation against light. Compared to the regions of the middle openings, the regions around the end openings are not as thick to fit protrusion of the ears, whereby to achieve better insulation against noise, and to create a quieter environment for enjoying of desired music selected from the user from the speakers.

Figure 7A:
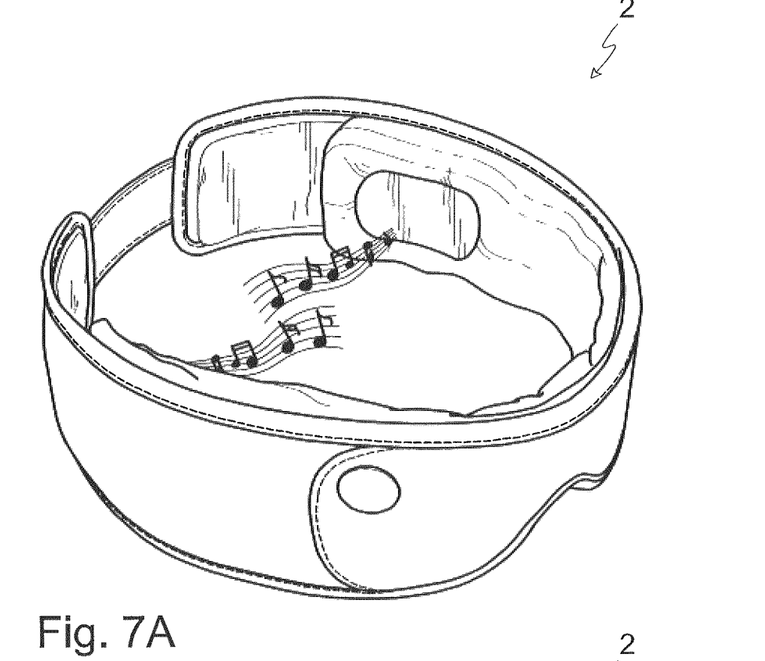
FIGS. 7A and 7B are perspective view of the shield of FIG. 1 but in a second configuration.
Figure 7B:
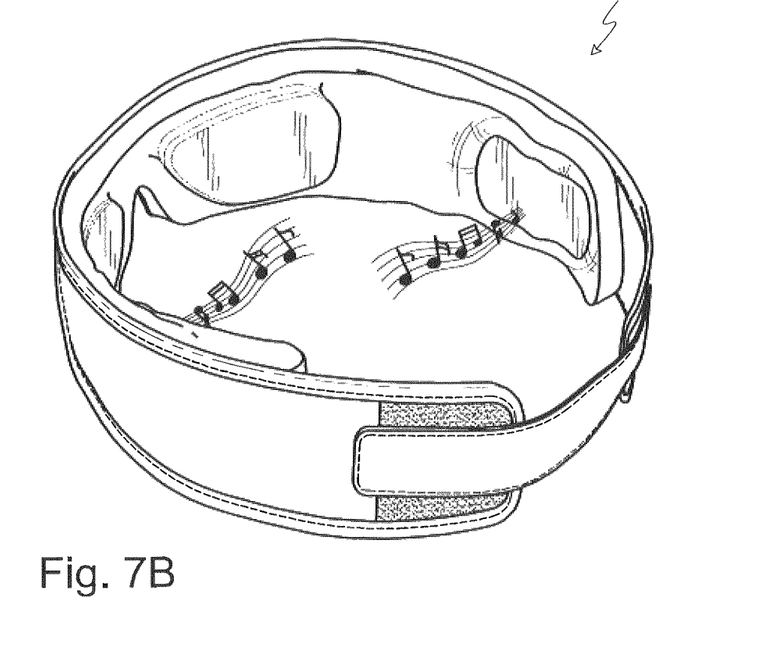

FIGS. 7A and 7B are front perspective views and rear perspective views of the shield in a closed configuration as if it, is being used by a user. It is envisaged that in this configuration, while the shield 2 is worn by a user, desired sound or music of choice by the user is played from the speakers. Since different users have different circumferential profile around the eye and ear region, a user can adjust the position of the speakers arranged between the body and the cushion before wearing the shield. It is envisaged that some users may prefer to position the speakers right on or closer to the ears, while other may prefer to locate the speakers behind the ears or closer to the eyes, e.g. at the temple regions. The shield 2 provides this flexibility allowing the user to place the speakers at desired locations on the between the body and the cushion.

Figure 8:
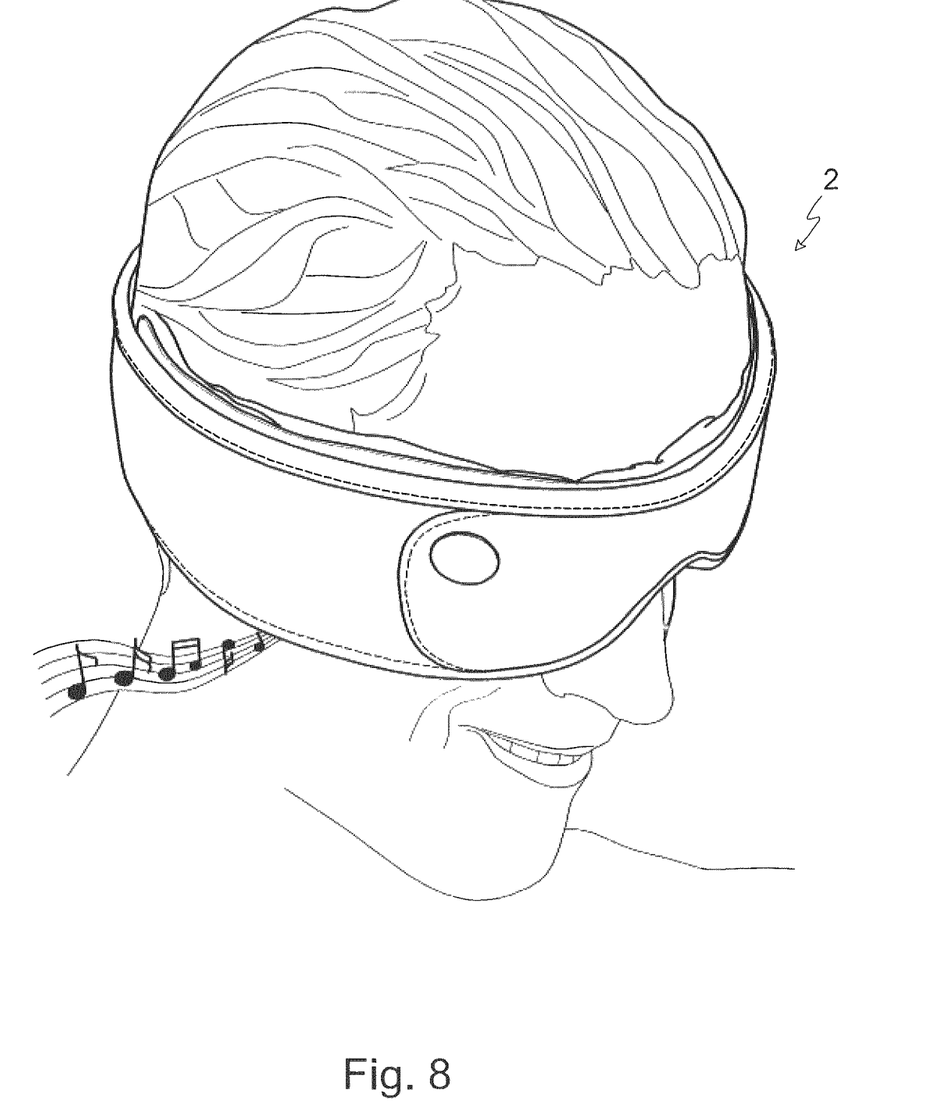
FIG. 8 is a schematic view of the shield of FIG. 1 or 4 when worn by a user during operation.

FIG. 8 shows the shield 2 in by a user. It is envisaged that the shield has a number of functionalities which together provides a means for temporary escape heaven. First, the eye cover regions cover the eyes and insulate the user from surrounding light. Second, the ear cover regions cover the ears and insulate the user from surrounding sound or noise. Further, the location of the speakers is adjustable to fit the needs of the user.

Figure 9A:
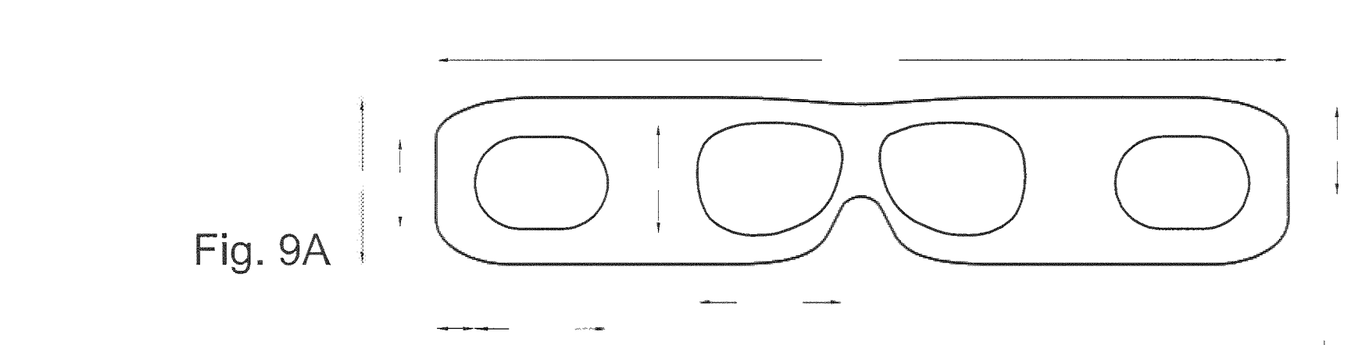
FIGS. 9A, 9B and 9C are schematic views of a cushion of a third embodiment of a combination ear and eye shield according to the present invention.
Figures 9B, 9C:
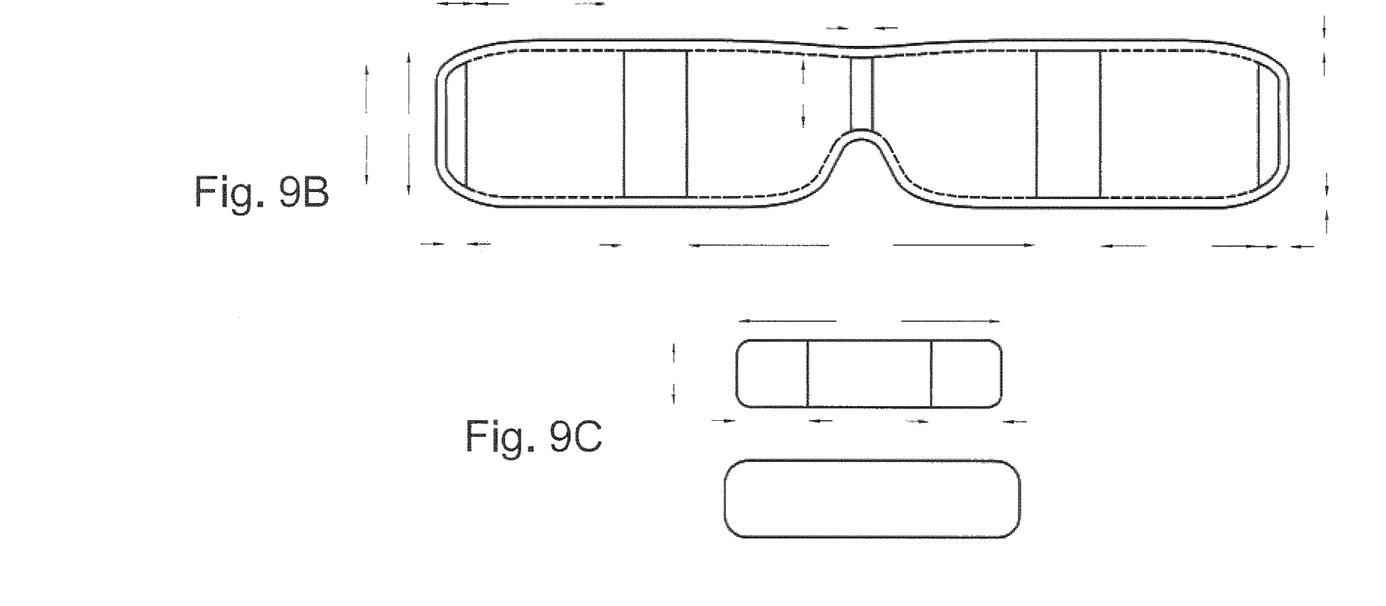

FIGS. 9A, 9B and 9C are schematic views of a cushion of a third embodiment of a combination ear and eye shield according to the present invention. Specifically, FIG. 9A illustrates the configuration of the cushion defining openings at which the eyes and the ears engages in which. FIG. 9B illustrates a chassis to which the cushion is secured. The chassis is provided with removably attachable adhesion means, such as coarse/loop elements or Velcro members to which the cushion is secured. FIG. 9C illustrate a connecting strap.

Figure 10A:
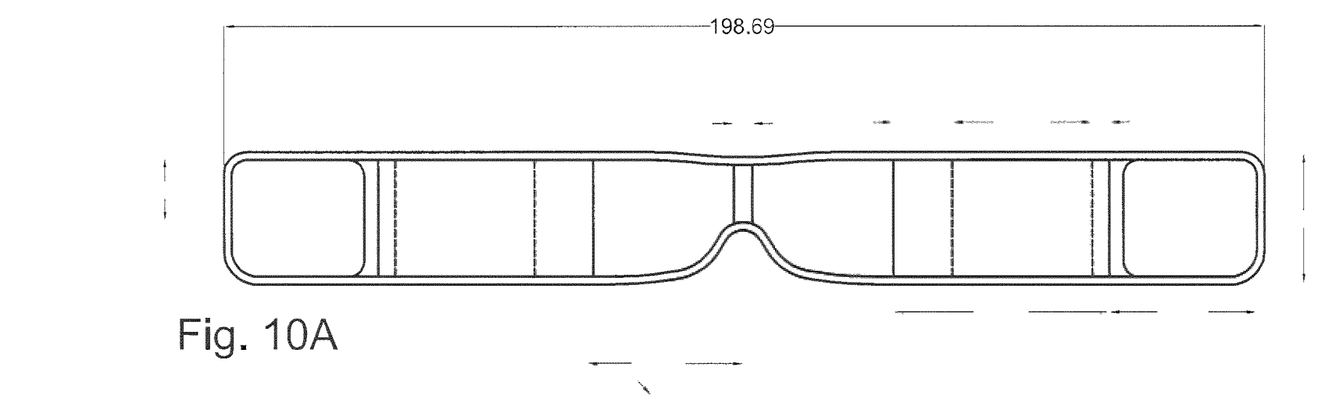
FIGS. 10A, 10B and 10C are schematic views of an outwardly facing portion of the combination ear an eye shield referred to in FIGS. 9A, 9B and 9C.
Figure 10B:
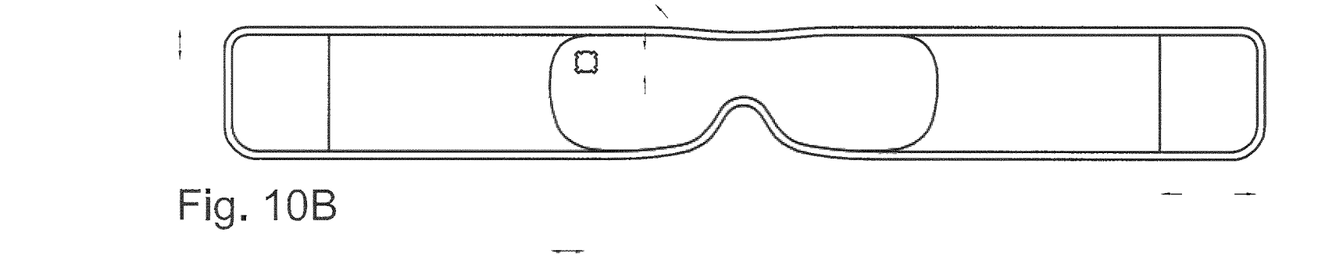
Figure 10C:
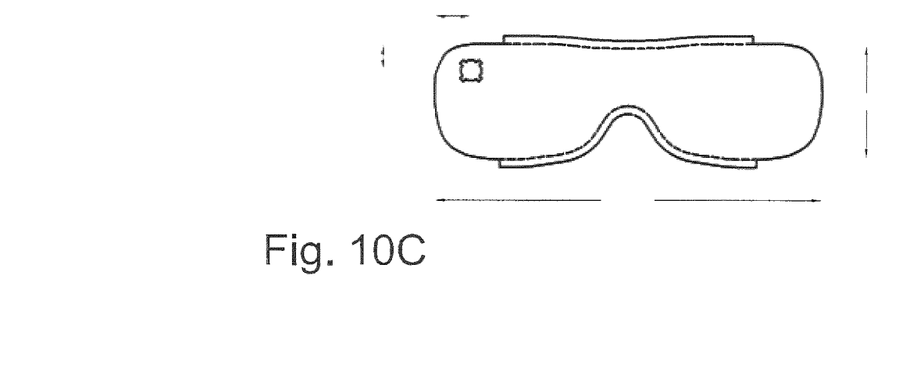

10A, 10B and 10C are schematic views of an outwardly facing portion of the combination ear an eye shield referred to in FIGS. 9A, 9B and 9C. The outwardly facing portion incorporates the chassis as shown in FIG. 9B, as shown in FIG. 10A. FIG. 10B illustrates the appearance on the outwardly facing side of the combination ear an eye shield. FIG. 10C illustrates a centre member of the outwardly facing portion stitched or otherwise secured to the outwardly facing surface of the outwardly facing portion. The centre member, among other roles, serves to enhance light blocking of the shield.

Figure 11A:
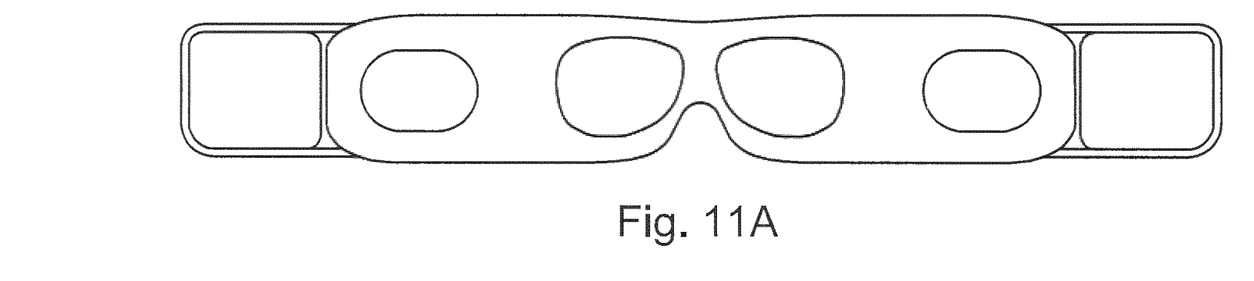
FIGS. 11A and 11B are schematic views of the combination ear an eye shield referred to in FIGS. 9A to 10C.
Figure 11B:
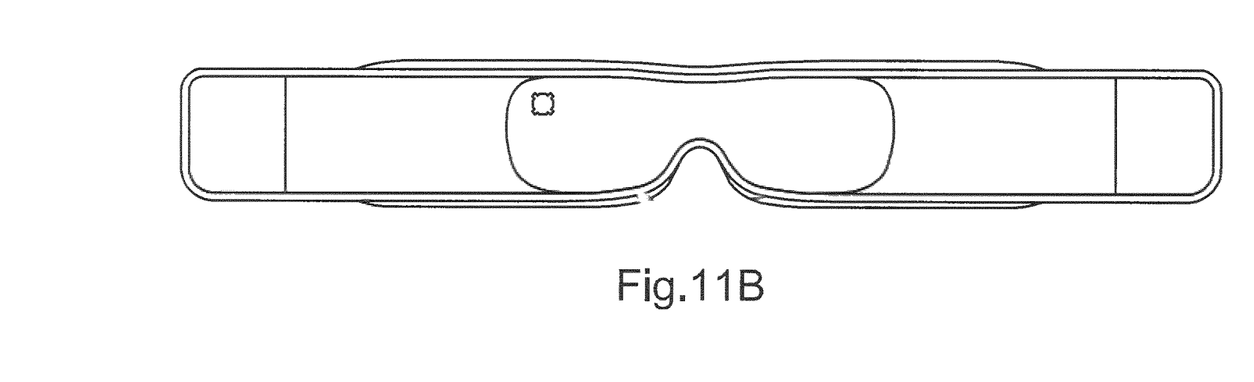

FIGS. 11A and 11B are schematic views of the combination ear an eye shield referred to in FIGS. 9A to 10C. FIGS. 11A and 11B shows the state of the shield when the cushion, the chassis and the outwardly facing portion are assembled.

Although not shown in the figures, an embodiment of the present invention is concerned with an audio and visual system comprising such shield (e.g. shield 2 or 32) and a portable electronic device such as smart phone. The electronic device is loaded with an application via which a user can interface and control the speakers. The electronic device is either loaded with sound or music files or is accessible to sound or music files stored in a remote location (e.g. in a cloud drive or a remote server). The portable device is communicable with the transceiver wirelessly, e.g. by way of a Bluetooth connection. Before a user requires a time-out session use the system s/he would first turn on the transceiver and the portable device and establish wireless connection between the portable device and the transceiver. Then the user via the application determine the sound or music s/he would like to listen to during the time-out session, and then wear the shield around the eye and ear region. It is to be noted that a person skilled in the art of portable devices, smart phone apps, and wireless communication would be able to understand the aspects of sound/music file storing, smart device applications and wireless communication, and is able to implement the invention as depicted above.

It should be understood that certain features of the invention, which are, for clarity, described in the content of separate embodiments, may be provided in combination in a single embodiment. Conversely, various features of the invention which are, for brevity, described in the content of a single embodiment, may be provided separately or in any appropriate sub-combinations. It is to be noted that certain features of the embodiments are illustrated by way of non-limiting examples. Also, a skilled person in the art will be aware of the prior art which is not explained in the above for brevity purpose.

The invention claimed is:

1. A combination ear and eye shield comprising:
 a) an elongate and continuous body wearable by a user defining, in use, an outwardly facing surface and an inwardly facing surface, the body having a height of 64-96 mm;
 b) one continuous cushion with an elongate profile, the continuous cushion being shorter in length and taller in height than the body and with a length of 360-540 mm and a height of 71.4-107 mm such that the cushion extends and protrudes upwardly and downwardly beyond the body;
 c) a closure member for removably connecting free ends of the body together, and lateral ends of the cushion are not connected together;
 d) the cushion is removably adhered to the inwardly facing surface of the body;
 e) a pair of speakers;
 f) an audio signal transceiver connectable to the speakers for transmitting audio signals thereto; and
 g) a power supply to power the transceiver and/or the speakers;
 wherein:
 i) the one continuous cushion includes both ear covering regions to cover both ears of a user and eye covering regions for covering both eyes of the user for providing improved light and sound insulation from the surroundings;
 ii) the transceiver is wirelessly communicable with an external device for receiving audio signals of desired sound or music;
 iii) the speakers are removably connectable to the inwardly facing surface of the body and locus changeable along the body, and interposable between the elongate continuous body and the cushion such that the speakers are adjustable in position adjacent the ears of a user; and
 iv) a first fastener for removable connection of the speakers to the body.

2. A shield as claimed in claim 1, wherein the elongate body is configured to assume a first configuration with a straightened profile, or a second configuration, and wherein in the first configuration the free ends of the body are disengaged.

3. A shied as claimed in claim 2, wherein in the second configuration the body is closed by the closure member for connecting the free ends thus to allow the shield to form a closed loop surrounding both the ears and the eyes of a user.

4. A shield as claimed in claim 3, wherein in the second configuration the speakers are arranged on opposite sides of the loop shaped shield.

5. A shield as claimed in claim 3, comprising a second fastener for stowing the transceiver, wherein, in the first configuration, the eye covering regions are interposed between the ear covering regions or speakers.

6. A shield as claimed in claim 5, wherein, in the first configuration, the transceiver is positioned at a distal end of the body.

7. A shield as claimed in claim 1, wherein the first fastener is in the form of hook structures and cooperative coarse loop structures on the speakers and the body, respectively, or vice versa.

8. A shield as claimed in claim 1, wherein the body is provided with a plurality of recesses or pockets along the length thereof for accommodating the speakers.

9. A shield as claimed in claim 1, comprising a second fastener for stowing the transceiver, wherein the second fastener is in the form of a pouch sized and shaped to fit the transceiver.

10. A shield as claimed in claim 1, wherein the cushion is provided with first and second openings on opposite distal ends thereof, the openings are sized and shaped to receive the speakers and/or to position over the ears in use.

11. A shield as claimed in claim 10, wherein the cushion is provided with third and fourth openings defining a rim and sized and shaped to fit around eye sockets of the eyes in use.

12. A shield as claimed in claim 1, wherein the power supply is in the form of a battery, wherein the battery is chargeable.

13. An audio and visual shield system comprising,
 a) a combination ear and eye shield as claimed in claim 1; and
 b) an or the external electronic or portable device communicable with the transceiver;
 wherein the external device stores sound or music files or access to sound or music files in a remote location, and acts as an interface via which a user can control which of sound or music files is played and thus broadcasted by the speaker(s).

14. A system as claimed in claim 13, wherein the external device is a mobile phone or a tablet.

15. A system as claimed in claim 13, comprising an application comprised in or loaded to the external device acting an interface via which a user can control the system of the shield.

16. A combination ear and eye shield comprising:
 a) an elongate and continuous body wearable by a user defining, in use, an outwardly facing surface and an inwardly facing surface, the body having a height of 64-96 mm;
 b) one elongate and continuous cushion with the cushion being shorter in length than the body and with a length of 360-540 mm and a height of 71.4-107 mm;
 c) the cushion is taller in height than the body, extends and protrudes upwardly and downwardly beyond the body, and is removably adhered to the inwardly facing surface of the body;
 d) a closure member for removably connecting free ends of the body together;
 e) at least one speaker positioned between the elongate body and the cushion, the speaker connectable to the inwardly facing face of the body and positionable between the body and the cushion;
 f) an audio signal transceiver connectable to the speaker for transmitting audio signals thereto; and
 g) a power supply to power the transceiver and/or the speaker;
 wherein:
 i) the one elongate and continuous cushion includes both ear covering regions to cover both the ear and eye covering regions for covering both the eyes;
 ii) the transceiver is wirelessly communicable with an external device for receiving audio signals of desired sound or music;

iii) the at least one speaker is removably connectable to and locus changeable along the body whereby the at least one speaker is adjustable in position adjacent one of the ears of a user or at a position desired by the user; and
iv) the shield further comprises a first fastener for removable connection of the at least one speaker to the body.

\* \* \* \* \*